United States Patent [19]

Knowles, Jr. et al.

[11] Patent Number: 5,575,988
[45] Date of Patent: Nov. 19, 1996

[54] COMBINATION SUNSCREEN AND INSECT REPELLENT

[75] Inventors: John H. Knowles, Jr., Essex; John C. Niles, Marblehead, both of Mass.

[73] Assignee: LittlePoint Corp., Wakefield, Mass.

[21] Appl. No.: 418,766

[22] Filed: Apr. 7, 1995

[51] Int. Cl.$^6$ ............ A61K 7/42; A61K 34/16; A61K 31/165
[52] U.S. Cl. ............ 424/59; 424/60; 424/DIG. 10; 514/617
[58] Field of Search ............ 424/DIG. 10, 60, 424/59

[56] References Cited

U.S. PATENT DOCUMENTS

| | | | |
|---|---|---|---|
| 3,186,912 | 6/1965 | Beamer | 167/91 |
| 3,594,481 | 7/1971 | Lindberg et al. | 424/258 |
| 3,821,363 | 6/1974 | Black et al. | 424/59 |
| 3,918,612 | 11/1975 | Voulgaris | 222/144.5 |
| 4,133,833 | 1/1979 | Hull | 260/558 R |
| 4,335,104 | 6/1982 | VanCleave | 424/59 |
| 4,529,598 | 7/1985 | Wong | 514/277 |
| 4,756,905 | 7/1988 | Melnik | 424/63 |
| 4,820,508 | 4/1989 | Wortzman | 424/59 |
| 4,895,727 | 1/1990 | Allen | 424/642 |
| 4,960,771 | 10/1990 | Rajadhyaksha | 514/228.8 |
| 4,963,591 | 10/1990 | Fourman et al. | 514/944 |
| 5,000,947 | 3/1991 | Nichols | 424/69 |
| 5,173,303 | 12/1992 | Lau et al. | 424/450 |
| 5,204,090 | 4/1993 | Han | 424/59 |
| 5,227,406 | 7/1993 | Beldock et al. | 514/703 |
| 5,290,570 | 3/1994 | Nichols | 424/499 |
| 5,346,922 | 9/1994 | Beldock et al. | 514/703 |

FOREIGN PATENT DOCUMENTS

| | | | |
|---|---|---|---|
| 0492007A1 | 7/1992 | European Pat. Off. | B01J 13/04 |
| 59-199602A | 11/1984 | Japan | A01N 2/08 |
| 5-92915A | 4/1993 | Japan | A61K 7/40 |
| WO94/00104 | 1/1994 | WIPO | A61K 7/42 |

*Primary Examiner*—Shelley A. Dodson
*Attorney, Agent, or Firm*—Testa, Hurwitz & Thibeault, LLP

[57] ABSTRACT

A combination sunscreen and insect repellent which is free of organic chemical sunscreens is disclosed. The composition contains an inorganic micronized inorganic substance and DEET. The sunscreen/insect repellent formulations described herein permit high loadings of inorganic sunscreen for improved performance. The composition can be applied topically as a lotion or cream.

14 Claims, No Drawings

5,575,988

COMBINATION SUNSCREEN AND INSECT REPELLENT

BACKGROUND OF THE INVENTION

Formulations that combine sunscreen activity and insect repellency have been described previously. See, U.S. Pat. Nos. 3,186,912; 4,963,591; PCT Appl. No. WO94/00104; U.S. Pat. No. 4,756,905; Japanese Appl. No. 59-199602; U.S. Pat. Nos. 5,204,090; 5,346,922; 3,594,481; Japanese Appl. No. 5-92915; U.S. Pat. No. 3,918,612 and EP Patent Appl. No. 0492007. N,N-diethyl-m-toluamide (deet) is used for insect repellency in many of these formulations due to its effectiveness, persistent activity and low toxicity. Many currently available formulations employ either an organic chemical sunscreen, a combination of organic chemical sunscreens or a combination of an inorganic sunscreen, such as zinc oxide (ZnO) or titanium dioxide ($TiO_2$), and organic chemical sunscreens to block ultraviolet (UV) radiation. Combinations of sunscreens often are necessary to achieve an effectively high skin protection factor (SPF) value.

Formulations containing combinations of deet and inorganic metal oxide powders such as $TiO_2$ previously have been described. For example, U.S. Pat. No. 4,756,905 discloses an opaque material containing a combination of deet and $TiO_2$ in which the metal oxides in the formulation were intended to act as pigments for camouflage. Japanese Patent No. 59-199602 discloses use of $TiO_2$ as a complexing agent with deet to retard skin absorption of deet and extend its repellency. In both instances, the $TiO_2$ present in the formulation could not act as a sunscreen agent because of its particle size, and because the amount of $TiO_2$ was not sufficient to provide an effectively high SPF. The $TiO_2$ described in these patents was a standard pigment grade form of $TiO_2$, which is not desirable because it appears white against the skin.

It is an object of this invention to provide improved combination sunscreen/insect repellent formulations for application to the skin that avoid the shortcomings of the prior art, in particular, which do not contain organic chemical sunscreen agents.

It is a further object of this invention to provide stable formulations that utilize high levels of micronized ZnO or $TiO_2$, or mixtures thereof, for sunscreen protection, in combination with deet as the insect repelling agent.

SUMMARY OF THE INVENTION

The invention relates to combination sunscreen and insect repellent formulations for topical application to human skin in which deet is the sole insect repellent and micronized, inorganic metal oxide is the sole sunscreen. More particularly, the invention relates to a composition comprising an insect repelling amount of an insect repellent consisting essentially of deet, and an effective sunblocking amount of a sunscreen consisting essentially of micronized titanium dioxide ($TiO_2$), zinc oxide (ZnO), or a mixture of $TiO_2$ and ZnO.

In a preferred aspect, formulations for topical application to the skin are formed in which the deet/$TiO_2$/ZnO composition is disposed in a cosmetically acceptable carrier, such as an aqueous solution, lotion, cream or gel. In a preferred embodiment, an emulsion, dispersion or suspension is formed in which deet and micronized $TiO^2$ and/or ZnO are dispersed in an aqueous base with emulsifying agents. Formulations having an aqueous emulsion base are preferred because they exhibit desirable characteristics such as enhanced viscosity, an even spread and smooth feel upon application to the skin. An emulsifying agent preferably is included to form a stable emulsion or dispersion of the oil-soluble deet and $TiO_2$ or ZnO. In the absence of the emulsifying agent, these ingredients may separate from the aqueous phase after mixing. The emulsifying agent aids formation of a stable dispersion of the oil-soluble components in the aqueous phase. The emulsion optionally may contain other ingredients including, for example, fragrances, coloring agents, emollients, moisturizers, thickeners or preservatives.

A process for preparing the insect repellent/sunscreen formulations also is the subject of the present invention. The process comprises the steps of combining an insect repelling amount of deet and an effective sunscreen amount of $TiO_2$ and/or ZnO, an emulsifying agent and water, and mixing the ingredients under conditions sufficient to form a stable emulsion. In another embodiment, water, an emulsifying agent and a thickener are combined to form an emulsion, and then deet and micronized metal oxide are mixed into the emulsion thereby forming a stable formulation. Additional ingredients may be added to the emulsion either during the emulsification step or after the emulsion is formed.

The composition and method of the present invention can be used to provide an effective insect repellent and sunscreen without the use of organic chemical sunscreens. Emulsion formulations prepared in accordance with the invention are stable, and can be prepared to contain high loadings of deet and $TiO_2$ and/or ZnO, thereby providing high levels of insect repellency and SPF values in a topically applicable, cosmetically pleasing form.

DETAILED DESCRIPTION

Deet (N,N-diethyl-m-toluamide) is readily commercially available, for example, from Morflex Chemical, Inc. The amount of deet which may be included in the compositions of the invention is from about 0.5% by weight to about 95% by weight. Preferably, the amount of deet will be in the range of from about 0.5% by weight to about 30% by weight. A concentration of from about 5% by weight to about 30% by weight is most preferred.

The $TiO_2$ and ZnO used in the instant invention are micronized, that is pulverized or ground to form very small particle size powders. The term "micronized" as used herein denotes finely ground particulate materials having a particle size of 10 microns (µ) or less. Micronized $TiO_2$ and ZnO preferred for use in the present compositions are those having a particle size of from about 5 nanometers (nm) to about 10µ, preferably about 0.3µ or less. $TiO_2$ and ZnO having a particle size of 0.3µ or less can be suspended in a formulation for topical application that renders it invisible on the skin. A more preferred range of particle size is from about 10 nm to about 30 nm. The amount of $TiO_2$ or ZnO, or mixture thereof, in the composition preferably is from about 0.5% by weight to about 30% by weight. A preferred range is from about 3% to 15% by weight, most preferably from about 4% to about 9% by weight. Micronized $TiO_2$ and ZnO are commercially available, as powders or in slurry form, for example from Presperse, Inc.

Water-dispersible $TiO_2$ having a particle size of between 10–30 nm is particularly preferred for use in the present invention. $TiO_2$ having a hydrophobic coating also can be used. The hydrophobic coating typically comprises silica, silicone, aluminum oxide or a combination of two or more of these. Water-dispersible and oil-dispersible $TiO_2$ are commercially available, for example from Tioxide Specialties, Ltd. The small particle size gives this form of $TiO_2$ optimum UV blocking and compatibility with deet.

In the present compositions, the micronized metal oxide, $TiO_2$ and/or ZnO, is used as the sole sunscreen agent, that is, all sunscreen activity in the composition is due to the presence of the metal oxide. In this instance, the concentration of metal oxide preferably is at least 2% by weight. Concentrations below 2% by weight may not provide SPF levels high enough for consumer needs.

$TiO_2$ and ZnO have the advantage of being odor free. The use of organic chemical sunscreens, such as benzoates, silicylates and anthranalates, generally imparts an undesirable chemical odor to the formulation. In addition, organic chemical sunscreens tend to complex with deet, resulting in unstable compounds that adversely effect the stability of the emulsion. Therefore, organic chemical sunscreens typically can not be used with deet to prepare a safe, high SPF, stable and cosmetically appealing insect repellent/sunscreen product. However, a formulation with all of these attributes can be prepared using micronized metal oxides, particularly $TiO_2$ and/or ZnO, in combination with deet.

In a preferred aspect of the present invention, the deet/$TiO_2$/ZnO are formulated into a cosmetically acceptable carrier such as an aqueous solution or emulsion or dispersion, cream, gel or lotion for topical application to the skin. The formulation also may be in the form of a pump spray or aerosol. Emulsions are useful as carriers for this purpose, including both water-in-oil or oil-in-water emulsions. Aqueous emulsions (oil-in-water emulsions) are the preferred vehicle for topical creams, gels and lotions due to their smooth feel, viscosity, spreadability and moisturizing effect. Generally, particulate metal oxides like $TiO_2$ and ZnO are difficult to stabilize at levels above 8% in aqueous emulsions. Levels of metal oxide above 8% by weight are preferred, however, to achieve SPF values above 15, which is the desired level. However, stable aqueous emulsion formulations made in accordance with the present invention can be prepared containing up to 30% by weight $TiO_2$ and/or ZnO. Emulsion formulations useful in the present invention typically contain from about 10% by weight to about 80% by weight water, preferably between about 30% by weight and 70% by weight water.

The process of emulsification is well known, and a number of emulsifying agents are commercially available. These agents all share a common molecular structure, having both hydrophilic (affinity for water) and hydrophobic (affinity for oils) regions within the same molecule. Emulsifying agents which can be used in the present invention include cationic, nonionic and anionic surface active agents, detergents, protein or carbohydrate polymers, long chain alcohols, fatty acids, fatty acid derivatives and soaps. The amount of emulsifying agent present in the formulation will vary, but typically in the range of 0.01% to about 10% by weight. Lipids, including oils, fatty alcohols, fatty acids and fatty acid derivatives, are preferred due to their low cost, low toxicity and good feel on the skin. Emulsifiers which are useful in the present invention include lecithin, octyl dodecanol, octyl palmitate and isopropyl myristate, for example.

Materials which thicken aqueous emulsions optionally may be added to the formulations of the present invention to achieve the desired consistency. Materials useful as thickening agents include, for example, cellulosic polymers such as ethyl cellulose, fatty alcohols such as octyl, stearyl, or cetostearyl alcohol, and various waxes or clays. Thickeners useful in topical cosmetics are well known and commercially available. The amount of thickening agent added will depend on the level of consistency desired.

The emulsion optionally may contain other ingredients including, for example, fragrances, coloring agents, oils, emollients, moisturizers, super fatting agents, softeners, preservatives, or any other compatible ingredients typically employed in topical cosmetics.

A process for preparing the insect repellent/sunscreen formulations also is the subject of the present invention. In one embodiment, the process comprises the steps of combining an insect repelling amount of deet and an effective sunscreen amount of $TiO_2$ and/or ZnO, an emulsifying agent, water, and mixing the ingredients under conditions sufficient to form a stable emulsion. Additional ingredients, such as preservatives, fragrances or thickeners, may be added to the emulsion either during the emulsification step or after the emulsion is formed.

In a preferred embodiment of the present process, water, emulsifying agent, deet and an oil mixed at a temperature and for a time sufficient to form an emulsion. The temperature typically is in the range of from about 50° C. to about 80° C. Mixing is carried out in a homogenizer, for example, until a stable emulsion or dispersion is achieved. The formed emulsion is allowed to cool while stirring is maintained. Once the temperature falls below about 50° C., the $TiO_2$ and/or ZnO are added to the emulsion or dispersion at the desired levels. The metal oxides may be added as powders, or may be predispersed in oil or water. The emulsion including the metal oxide then is stirred until a smooth, stable dispersion is achieved. Optional additives may be added at this time if desired, including, for example, preservatives, flagrance, coloring agents, emollients, etc., to form the topically applicable insect repellent/sunscreen formulation.

In another embodiment of the present process, water, a thickening agent and an emulsifying agent are mixed under conditions sufficient to form a thickened emulsion. Deet and $TiO_2$ and/or ZnO then are added to this emulsion at the desired levels to form the topically applicable insect repellent/sunscreen formulation. Additional ingredients, such as fragrances or coloring agents, optionally may be added.

The present composition and process provides an effective combination insect repellent and sunscreen, in which both the insect repellent and the sunscreen are contained in a unique emulsion matrix. The resulting material is cosmetically appealing, stable over time and contains no organic chemical sunscreens. The present formulations are used topically by an individual by smoothing onto the skin to form a protective film which has both insect repelling and sunscreen properties.

The invention further is illustrated by the following examples, which are not intended to be limiting in any way.

EXAMPLES

Example 1

A combination insect repellent/sunscreen formulation in accordance with the present invention was formed as follows:

| Formula 1 | |
|---|---|
| Water | 67.70% |
| Lecithin | 5.00 |
| Vegetable Oil | 12.50 |
| Potassium Phosphate | 0.18 |
| Sodium Phosphate | 0.74 |
| Methyl Paraben | 0.13 |
| Propyl Paraben | 0.05 |
| Dowacil (quaternium-15) | 0.20 |
| Deet | 6.50 |
| TiO$_2$ (micronized) | 7.00 |
| Total | 100.00% |

Water, vegetable oil, lecithin, deet, potassium phosphate, sodium phosphate, methyl paraben and propyl paraben were combined and heated to about 72° C. The ingredients were mixed using a high shear homogenizer. Mixing was carried out until a stable dispersion was achieved. The emulsion was allowed to cool while stirring was continued. Once the temperature dropped below 50° C., an aqueous dispersion of TiO$_2$ was added, and stirring was continued until the ingredients were thoroughly mixed. Finally, the Dowacil (preservative) was added and mixing continued until thoroughly mixed. The resulting material was a stable emulsion in the form of a smooth lotion.

Example 2

The following formula may be used to form a combination insect repellent/sunscreen formulation in accordance with the present invention:

| Formula 2 | |
|---|---|
| Water | 28.30 |
| Cetyl Dimethicone Copolyol | 2.00 |
| Mineral Oil | 5.00 |
| Isohexadecane | 5.00 |
| Caprylic-capric Triglyceride | 5.00 |
| Octyl Palmitate | 8.00 |
| PPG-15 Stearyl Ether Cyclomethicone | 5.00 |
| Glyceryl Hydroxystearate | 0.80 |
| Ozokerite Wax | 1.20 |
| Sodium Chloride | 0.50 |
| Preservative | 0.20 |
| TiO$_2$ (micronized) | 18.00 |
| Deet | 21.00 |
| Total | 100.00 |

Example 3

The following evaluation of sun protection by SPF determination was carried out by AMA Laboratories, Inc. (New City, N.Y.). Evaluation of sun protection by SPF determination used TiO$_2$ Tioxide 50 nm. The test was carried out to evaluate the effectiveness of a test material as a sunscreen product by determining the Sun Protection Factor (SPF) on human skin as described in the Federal Register, Volume 43, Number 166, Food and Drug Administration entitled "Sunscreen Drug Products for Over-The-Counter Human Use", Part II, Aug. 25, 1978, pages 38259 through 38262, using a Xenon arc solar simulator as the UV source.

SAMPLE DESCRIPTION

Two samples made in accordance with Example 1 were tested. The test samples utilized TiO$_2$ obtained from TiOxide Specialties Ltd. and had a particle size of approximately 50 nm. These samples were designated Sample 1 and Sample 2.

| PANEL DESIGN: | Number of subjects enrolled | 5 |
|---|---|---|
| | Number of subjects completing study | 5 |
| | Age Range | 19–51 |
| | Sex | |
| | Male | 2 |
| | Female | 3 |
| | Race | |
| | Caucasian | 5 |
| | Hispanic | 0 |
| | Asian | 0 |

The following evaluation of sun protection by SPF determination was carried out by AMA Laboratories, Inc. (New City, N.Y.). Evaluation of sun protection by SPF determination used TiO$_2$ Tioxide 50 nm. The test was carried out to evaluate the effectivenesss of a test material as a sunscreen product by determining the Sun Protection Factor (SPF) on human skin as described in the Federal Register, Volume 43, Number 166, Food and Drug Administration entitled "Sunscreen Drug Products for Over-The-Counter Human Use", Part II, Aug. 25, 1978, pages 38259 through 38262, using a Xenon arc solar simulator as the UV source.

SAMPLE DESCRIPTION

Two samples made in accordance with Example 1 were tested. The test samples utilized TiO$_2$ obtained from TiOxide Specialties Ltd. and had a particle size of approximately of 50 nm. These samples were designated Sample 1 and Sample 2. medical history form. These forms along with the signed consent forms, are available for inspection on the premises of AMA Laboratories, Inc. only. Reference 21 CFR Ch. 1 Part 50, Subpart B.

PANEL COMPOSITION:

Healthy volunteers over the age of 16 years were recruited for this study. The panel consisted of fair-skin individuals with skin types I, II or III defined as follows (Federal Register 43:38260, 1978).

Type I—Always burns easily; never tans (sensitive)

Type II—Always burns easily; tans minimally (sensitive)

Type III—Burns moderately; tans gradually (light brown—normal)

INSTITUTIONAL REVIEW BOARD:

Reference: CFR Title 21 Part 56, Subparts A, B, C and D. The IRB of AMA Laboratories, Inc. consists of 5 or more individuals, chosen from within the company for technical expertise and from the local community for lay interaction. The list of IRB members is kept on file at AMA Laboratories, Inc., and is available for inspection during the hours of operation.

LIGHT SOURCE:

The light source employed is a 150 watt Xenon Arc Solar Simulator[1] (Solar Light Co., Philadelphia, Pa., Model 12S, Model 14S or Model 600) having a continuous emission spectrum in the UV-B range from 290 to 320 nm. Xenon arc is selected on the basis of its black body radiation temperature of 6000° K. which produces continuous UV spectra (all wavelengths) substantially equivalent to that of natural sunlight.

This device is equipped with a dichroic mirror (which reflects all radiation below 400 nm) and works in conjunction with a 1 mm thick Schott WG-320 filter (which absorbs all radiation below 290 nm) to produce simulation of the solar UVA-UVB spectrum. A 1 mm thick UG 5 or UG 11 filter (black lens) was added to remove reflected (infra-red, greater than 700 nm) heat and remaining visible radiation.

UVB radiation was monitored continuously during exposure using a Model DCS-1 Sunburn UV Meter/Dose Controller System (Solar Light Co.) formerly known as the Robertson-Berger Sunburn meter (R-B meter). Measurements were taken at a position within 8 mm from the surface of the skin. The field of irradiation was 1 cm in diameter.

Realignment of the Light Sources and calibration of the sunburn meters are conducted semi-annually by independent certification facilities and more often as necessary at the discretion of the operating technician or Study Director. 1/Berger, D.S.: Specification and design of solar ultraviolet simulators. *J. Invest. Dermatol.* 53:192–199 (1969).

PROCEDURE:

SPF DETERMINATION (INCLUDING 8% HOMOSALATE STANDARD)

The procedure for this study is outlined in the Federal Register, Vol. 43:38264–38267, 1978. One test site area served to determine each subject's Minimal Erythema Dose (MED). This was executed by exposing the back to a series of timed incremental UV exposures at 25% intervals. The individual subject's MED is the shortest time of exposure that produces minimally perceptible erythema at 16 to 24 hours post irradiation. The test area is described as the infrascapular area of the back to the right and left of the midline. The homosalate standard was delivered to the test site through plastic volumetric syringes. The material was then evenly applied to a rectangular area measuring 5 cm×10 cm (50cm$^2$) for a final concentration of 2.0 mg/cm$^2$. Fifteen (15.0) minutes after application, a series of UV light exposures in 25% increments, calculated from previously determined MED's, bracketing the intended SPF was administered from the solar simulator to subsites within the treated area. On the actual day of testing another series of exposures similar to the one given on the previous day was administered to an adjacent untreated, unprotected area of the skin to re-determine the MED.

Another adjacent test site was then selected to perform an SPF determination on the test substance. When applicable, in-house high SPF standards are employed, at the discretion of the study director to maintain precision integrity within these ranges.

EVALUATION OF RESPONSES:

Sixteen to twenty-four hours post exposure, the volunteers are instructed to return to the testing facility for evaluation of delayed erythemic response. The smallest exposure or the least amount of energy required to produce erythema (MED) in the treated site was recorded. The SPF was then calculated according to the following equation:

$$SPF = \frac{MED \text{ Protected Skin}}{MED \text{ Unprotected Skin}}$$

REJECTION CRITERIA:

Panelist's results were rejected and the panelist replaced if:

1. The responses on the treated test site were randomly absent or out of sequence. This was an indication that the products were not spread uniformly.
2. An MED could not be obtained due to elicited response at all exposure sites.
3. The exposure series failed to elicit an MED response on either the untreated or the applied skin areas. The test was then considered a technical failure and the subject's data was discarded.

RESULTS: The results are shown in Tables:

TABLE 1

| Subject ID# | Sex | MED/HR | I (Amps) | Skin Type | MED (Sec) | STD (8% HMS) | SPF Value |
|---|---|---|---|---|---|---|---|
| 46 3749 | F | 25.0 | 7.0 | II | 8 | 4.50 | 13.75 |
| 66 9819 | M | 26.0 | 7.2 | III | 11 | 5.09 | 12.55 |
| 48 5165 | F | 25.0 | 7.0 | II | 6 | 4.83 | 14.67 |
| 34 1401 | F | 24.9 | 7.0 | II | 8 | 4.50 | 11.00 |
| 70 1472 | M | 25.2 | 6.8 | III | 11 | 5.09 | 10.00 |
| MEAN SPF: | | | | | | 4.80 | 12.39 |
| STANDARD DEVIATION: | | | | | | 0.30 | 1.92 |
| S.E. MEAN (S.E.M.): | | | | | | 0.13 | 0.86 |
| S.E. % OF MEAN | | | | | | 2.71 | 6.94 |
| N: | | | | | | 5 | 5 |

MED: Minimal Erythemal Dose
I: Intensity of light source

TABLE 2

Sample 2

| Subject ID# | Sex | MED/HR | I (Amps) | Skin Type | MED (Sec) | STD (8% HMS) | SPF Value |
|---|---|---|---|---|---|---|---|
| 46 3749 | F | 25.0 | 7.0 | II | 8 | 4.50 | 13.75 |
| 66 9819 | M | 26.0 | 7.2 | III | 11 | 5.09 | 15.64 |
| 48 5165 | F | 25.0 | 7.0 | II | 6 | 4.83 | 14.67 |
| 34 1401 | F | 24.9 | 7.0 | II | 8 | 4.50 | 17.25 |
| 70 1472 | M | 25.2 | 6.8 | III | 11 | 5.09 | 10.00 |
| MEAN SPF: | | | | | | 4.80 | 14.26 |
| STANDARD DEVIATION: | | | | | | 0.30 | 2.71 |
| S.E. MEAN (S.E.M.): | | | | | | 0.13 | 1.21 |
| S.E. % OF MEAN | | | | | | 2.71 | 8.49 |
| N: | | | | | | 5 | 5 |

MED: Minimal Erythemal Dose
I: Intensity of light source

OBSERVATIONS:

No adverse effects or unexpected reactions of any kind were observed on any of the subjects.

CONCLUSION:

The Sun Protection Factor (SPF) of the samples listed below, when tested on five subjects under static conditions as described herein, yielded the following SPF values:

| SAMPLE DESCRIPTION | SPF VALUE |
|---|---|
| Sample 1 | 12.39 |
| Sample 2 | 14.26 |

The mean SPF of the 8% homosalate standard in the same panel was 4.80.

Example 4

The following evaluation of insect repellency was carried out at the Harvard School of Public Health, Department of Tropical Public Health, Boston, Mass. Samples were made in accordance with Example 1. Three samples were tested, containing 6.5% DEET. The TiO$_2$ used in formulas was obtained from Presperse, Inc. and had a particle size of approximately 20 nm.

EFFICACY TESTS:

Test Substance Application:

The candidate DEET (N,N-Diethyl-m-toluamide, 6.5% v/v) formulations (6.5% DEET Lotion; 6.5% DEET Spritz; and 6.5 DEET+TiO$_2$ Sunscreen) were supplied in uniquely numbered, sealed bottles by the sponsor (LittlePoint Corporation). These were designated Sample 1, Sample 2 and Sample 3, respectively. The test substance was maintained at 22° C. in a secure laboratory, and was protected from extremes in temperature, light, radiation or other adverse conditions.

Immediately prior to testing, each bottle of test substance was vigorously agitated. An aliquant was then removed using a calibrated micropipette, and the specified amount was deposited and spread onto a volunteer's forearm within the prescribed patch.

Tests for repellency were conducted by spreading 50 mg of the candidate DEET formulation on a circular patch encompassing 15.90 cm$^2$ on a volunteer's forearm. At this application rate, each 15.90 cm$^2$ patch was treated with 3.25 mg DEET [(50 mg)*6.5 g/100 g]. Equivalent marked areas on the forearm were left untreated.

Efficacy test with mosquitoes:

Adult nulliparous female *Aedes aegypti* mosquitoes, between one and two weeks of age, were used to screen all test substances. The established colony was maintained by skilled laboratory personnel in a secure insectary maintained at 24° C. and 80% relative humidity on a 14L:10D photoperiodic cycle. Sucrose cubes were removed from the colony cages 24 hours prior to testing.

Groups of ten female mosquitoes were aspirated from the colony cage and loaded in Plexiglas test cages. Each test cage consisted of a cylinder 14 cm long with an internal diameter of 4.5 cm. The open area of the cylinder corresponded to the prescribed area of the test patch on the volunteer's forearm. One end of the test cage was closed by a neoprene stopper; the other end was covered by monofilament nylon mesh (tulle); each mesh opening measures approximately 1 mm square. Three test chambers were utilized for each test substance on each volunteer. Test cages were loaded with mosquitoes no more than 30 minutes prior to test initiation and were maintained within the secure and environmentally controlled insectary.

The mesh-covered end of a test cage was placed directly over the untreated patch on the skin. Responses of the mosquitoes were observed for one minute, or until at least two mosquitoes landed on the skin and began to probe (but not feed). Any test cage in which fewer than two mosquitoes landed and probed within one minute were discarded. A test cage in which at least two mosquitoes landed and probed was then removed from the untreated patch of skin and placed onto a treated patch on the same volunteer. Responses of the mosquitoes were observed for at least two minutes, or until at least one mosquito landed and began to probe the skin. Each test substance was thereby screened by exposing to at least two cages of mosquitoes at hourly intervals until the test substance has lost efficacy.

Repellent activity of each substance was gauged by two behavioral parameters. Landing and probing by the mosquitoes.

1) Stationary repose upon landing: DEET induces an avoidance behavior (decreased attractiveness) by mosquitoes to the treated surface. Thus, mosquitoes initially avoid such a surface by taking flight and/or tend not to alight on that surface. Such activity precludes any possibility of feeding. As repellency activity begins to wane, mosquitoes will begin to land, but will not attain a stationary repose. Instead, they clamber sideways in a crab-like manner as to avoid prolonged contact with the surface. Further loss of repellency activity is noted when mosquitoes maintain a stationary repose upon landing; only then is probing and feeding possible.

2) Probing: Probing activity is limited to those mosquitoes that have landed upon the skin and remain in a stationary attitude. Probing is confirmed by observing the mosquito's mouthparts enter the skin, by the associated sensation of this activity, and by the resulting reaction at the bite site.

From these data, the relative duration of repellent activity was determined. Repellent effectiveness is based on the duration of protection from probing, i.e. the period from test substance application until the first probe. Landing behavior is used solely as a redundant measure to confirm protection. At least three volunteers screen the candidate formulations on separate days with different groups of mosquitoes. The mean and median duration of protection was calculated from the overall results.

Results of tests, summarized below, reflect minimum repellent activity times; the actual duration of activity may exceed indicated values by 59 minutes.

TABLE 3

| Formulation | | Result of Mosquito Tests | | | | | | | Mean | SD | Median |
|---|---|---|---|---|---|---|---|---|---|---|---|
| | | Efficacy (hrs) per replicate Each column represents 1 volunteer | | | | | | | | | |
| Sunscreen | Land | 3 | 5 | 3 | 3 | 1 | 1 | 4 | 2.9 | 1.5 | 3 |
| Sample 3 | Probe | 4 | 5 | 3 | 3 | 1 | 2 | 4 | 3.1 | 1.3 | 3 |
| Spritz | Land | 2 | 2 | 2 | 1 | 2 | 2 | 2 | 1.9 | 0.4 | 2 |
| Sample 2 | Probe | 3 | 2 | 2 | 2 | 2 | 2 | 3 | 2.3 | 0.5 | 2 |
| Lotion | Land | 3 | 2 | 4 | 1 | 2 | 2 | 3 | 2.3 | 1.0 | 2 |
| Sample 1 | Probe | 3 | 2 | 4 | 2 | 2 | 2 | 3 | 2.6 | 0.8 | 2 |

Efficacy Tests with Ticks

Nymphal deer ticks, *Ixodes dammini*, were used to screen test substances. Nymphs were derived from a laboratory colony and were maintained in a secure insectary under at 24° C., 95% relative humidity and at a 14L:10D photoperiod.

Groups of ten or more unfed nymphal ticks were removed from the cage and placed onto an inverted 5-dram plastic vial. This vial was situated within a plastic petri dish bottom (3.5 cm diameter) glued in the center of a 9 cm plastic petri dish bottom. The moat thus formed between the two dishes was filled with water to prevent the escape of ticks from the center dish. Test dishes were loaded with ticks no more than 30 minutes prior to test initiation and were maintained within the insectary. Tests were performed in a secure and environmentally controlled insectary. Eight or more hours were allotted each day for testing.

At each test interval, the response of questing ticks to untreated skin was first determined. Thus, untreated skin was offered to questing ticks by gently brushing it near the forelegs of each tick. At least 60% of ticks so exposed must have attempted to crawl onto that skin surface in order for testing to proceed. Any test dish in which fewer than 60% of questing ticks failed to respond in this manner was discarded; this initial screening was then repeated with a new batch of ticks. Any ticks that crawled onto the untreated skin were immediately transferred back to the dish by gently grasping the rear leg with fine forceps. Each treated patch of skin was then similarly offered to such questing ticks. Finally, to confirm that questing ticks remained attached to untreated skin, the untreated skin was re-offered to each tick after exposure to the treated skin. Responses of the ticks were observed at approximately hourly intervals for at least 4 hours.

Repellent activity of each test substance was gauged by the responses of ticks after exposure to the test substance. From these data, the relative duration of repellent activity was determined. Repellent effectiveness is based on the magnitude of the period during which ticks fail to attempt to grasp the treated skin. Continued repellent failure at the next hourly time point was required for confirmation. At least three volunteers screened the candidate formulations on separate days with different groups of ticks. The median duration of protection was calculated from the results.

Results of test, summarized below, reflect minimum repellent activity times; the actual duration of activity may exceed indicated values by 59 minutes.

TABLE 4

| Formulation | Result of tick tests | | | | | | | Mean | SD | median |
|---|---|---|---|---|---|---|---|---|---|---|
| | Efficacy (hrs) per volunteer | | | | | | | | | |
| Sunscreen Sample 3 | 4 | 4 | 4 | 6 | 1 | 1 | 3 | 3.3 | 1.8 | 4 |
| Spritz Sample 2 | 4 | 4 | 4 | 6 | 1 | 2 | 3 | 3.4 | 1.6 | 4 |
| Lotion Sample 1 | 5 | 4 | 4 | 4 | 1 | 2 | 1 | 3.0 | 1.6 | 4 |

Equivalents

From the foregoing description, one skilled in the art can easily ascertain the essential characteristics of this invention, and without departing from the spirit and scope thereof, can make various changes and modifications to adapt it to various usages and conditions.

Such embodiments are intended to be included within the scope of the following claims.

We claim:

1. A combination insect repellent and sunscreen composition for topical application comprising:
   a. an amount of an insect repellent consisting essentially of N,N-diethyl-m-toluamide sufficient to repel insects when applied topically; and
   b. an amount of a sunscreen agent consisting essentially of micronized particles of titanium dioxide, zinc oxide or mixtures thereof sufficient to provide an effective sunscreen when applied topically.

2. The composition of claim 1 wherein the concentration of the insect repellent is in the range of from about 0.5% by weight to about 95% by weight of the composition.

3. The composition of claim 1 wherein the concentration of the sunscreen agent is in the range of from about 0.5% by weight to about 30% by weight of the composition.

4. The composition of claim 1 further comprising a carrier comprising an oil-in-water emulsion, or a water-in-oil emulsion.

5. The composition of claim 1 wherein the sunscreen has a particle size of about 10 microns or less.

6. The composition of claim 5 wherein the sunscreen comprises titanium dioxide having a particle size between about 10 and 30 nanometers.

7. A combination insect repellent and sunscreen composition for topical application comprising:
   a. an insect repelling amount of an insect repellent consisting essentially of N,N-diethyl-m-toluamide;
   b. an effective sunscreening amount of a sunscreen agent consisting essentially of micronized particles of titanium dioxide, zinc oxide or mixtures thereof; and
   c. a carrier comprising an emulsion.

8. The composition of claim 7 further comprising a thickening polymer.

9. The composition of claim 7 wherein the concentration of the insect repellent is in the range of from about 0.5% by weight to about 95% by weight of the composition.

10. The composition of claim 9 wherein the concentration of insect repellent is in the range of from about 5% by weight to about 30% by weight of the composition.

11. The composition of claim 7 wherein the concentration of the sunscreen is in the range of from about 0.5% by weight to about 30% by weight of the composition.

12. The composition of claim 11 wherein the concentration of the sunscreen is in the range of from about 2% by weight to about 9% by weight of the composition.

13. A process for preparing a combination insect repellent and sunscreen composition for topical application, comprising the steps of:
   combining N,N-diethyl-m-toluamide, and micronized particles of titanium dioxide or zinc oxide with an emulsifying agent and water; and mixing under conditions sufficient to form a stable emulsion.

14. A process for preparing a combination insect repellent and sunscreen composition for topical application, comprising the steps of:
   combining water, an emulsifying agent and N,N-diethyl-m-toluamide and mixing under conditions sufficient to form a stable base emulsion; adding to the formed base emulsion an effective sunscreen amount of micronized particles of titanium dioxide or zinc oxide, or mixture thereof, and mixing to form a stable emulsion.

* * * * *